United States Patent [19]
Flemming et al.

[11] Patent Number: 6,117,436
[45] Date of Patent: Sep. 12, 2000

[54] COSMETIC CARE PRODUCT WITH TWO COMPONENTS

[75] Inventors: Ernst Flemming, Heusenstamm; Ursula Hehner, Brensbach; Eckhard Wilhelm, Alsbach/Haehnlein, all of Germany; Ulrich Eicken, Fribourg; Sybille Jungo, Marly, both of Switzerland; Karl-Heinz Kischka; Friedel Schroeder, both of Darmstadt, Germany

[73] Assignee: Wella Aktiengesellschaft, Darmstadt, Germany

[21] Appl. No.: 09/297,285

[22] PCT Filed: Jul. 11, 1998

[86] PCT No.: PCT/EP98/04304

§ 371 Date: Jun. 28, 1999

§ 102(e) Date: Jun. 28, 1999

[87] PCT Pub. No.: WO99/11222

PCT Pub. Date: Mar. 11, 1999

[30] Foreign Application Priority Data

Aug. 28, 1997 [DE] Germany .......................... 197 37 536
Mar. 7, 1998 [DE] Germany .......................... 198 09 942

[51] Int. Cl.[7] .................. A61K 7/00; A61K 7/06; A61K 7/11; A61K 7/075; A61K 7/08
[52] U.S. Cl. .................. 424/401; 424/70.1; 424/70.12; 424/70.21; 424/70.22; 424/70.27; 424/70.31; 424/400; 514/937
[58] Field of Search .................. 424/400, 401, 424/70.1, 70.12, 70.21, 70.22, 70.27, 70.31; 514/937

[56] References Cited

U.S. PATENT DOCUMENTS

| | | | |
|---|---|---|---|
| 4,226,852 | 10/1980 | Tesmann et al. | 424/62 |
| 4,335,103 | 6/1982 | Barker et al. | 424/59 |
| 4,832,943 | 5/1989 | Grollier et al. | 424/59 |
| 4,980,155 | 12/1990 | Shah et al. | 424/63 |
| 5,059,414 | 10/1991 | Dallal et al. | 424/70 |
| 5,118,507 | 6/1992 | Clement . | |
| 5,213,799 | 5/1993 | Goring et al. | 424/401 |
| 5,250,289 | 10/1993 | Boothroyd et al. . | |
| 5,455,035 | 10/1995 | Guerroro et al. | 424/401 |
| 5,565,216 | 10/1996 | Cowsar et al. | 424/704 |
| 5,612,044 | 3/1997 | Suares et al. | 424/401 |
| 5,750,092 | 5/1998 | Meyer et al. | 424/59 |

FOREIGN PATENT DOCUMENTS

| | | |
|---|---|---|
| 0 641 557 A1 | 3/1995 | European Pat. Off. . |
| 0 705 593 A1 | 4/1996 | European Pat. Off. . |
| 0 719 539 A2 | 7/1996 | European Pat. Off. . |
| 0 728 460 A1 | 8/1996 | European Pat. Off. . |
| 0 662 816 B1 | 1/1997 | European Pat. Off. . |

OTHER PUBLICATIONS

Domsch, A.: Die Kosmetische Praeparate, Verlag fuer chemische Industrie (H. Ziolkowsky, Ed), 4. Aylage, Band, pp. 212–230, 1992.

Schrader, K.: Grundlagen Und Rezepten Der Kosmetika, 2. Auflage, 1989, pp. 728–737.

62–Essential Oils, Cosmetics, vol. 119, 1993, 55730, p. 423.

*Primary Examiner*—Shelley A. Dodson
*Assistant Examiner*—Marina Lamm
*Attorney, Agent, or Firm*—Michael J. Striker

[57] ABSTRACT

The cosmetic care preparation has a first component and a second component kept separate from the first component prior to application, which are mixed immediately prior to application on the hair and/or skin to form a ready-to-use product. The first component includes at least one conditioning ingredient, preferably one or more fats, oils and/or waxes, and the second component is a cationic or anionic base emulsion that includes at least one lipophilic substance, at least one cationic or anionic emulsifier, at least one organic acid and water. In a particularly preferred embodiment, the first component includes at least one cationic surfactant and/or at least one cationic polymer and the second component includes at least one monoalcohol and/or at least one amphoteric or nonionic surfactant. The first and the second components are mixed in a ratio of 20:1 to 1:20 to obtain the ready-to-use product but within that range of weight ratios the relative proportions of the first and second components can be adjusted to match a particular skin and/or hair type or quality.

27 Claims, No Drawings

COSMETIC CARE PRODUCT WITH TWO COMPONENTS

BACKGROUND OF THE INVENTION

1. Field of the Invention

The subject of the invention is a care preparation, in particular a hair care preparation, which is in the form of a two-component preparation, wherein the first component includes conditioners and the second component substantially includes typical non-conditioning cosmetic vehicle substances for foundation substances, and in which the components are separate until use and are present in mixed form in variable quantities in the final product.

2. Prior Art

The hair and skin are negatively affected in terms of their physical, chemical and morphological properties by factors of various kinds. In particular, the unprotected skin and the hair on the head are exposed constantly to climatic influences, such as humidity or temperature phenomena or the rays of the sun. Cosmetic treatments such as frequent bleaching, permanent waves and dyeing, and even frequent hair washing with oil-reducing surfactants damage the hair structure. The hair becomes brittle and loses its natural sheen. The hair damaged in this way becomes electrostatically charged when brushed or combed, and the roughened surface of the hair causes matting and tangling, making the hair hard to comb and hard to smooth out.

Such changes in the hair can be temporary and can vary constantly.

Along with these exogenous influences, which have a major influence on the condition of the skin and hair, the individual nature of the skin and hair also plays a very decisive role in their proper care and in the choice of a care preparation to be used for them. In different human populations, the hair in particular, because of its structure, also varies.

Another factor is that natural aging causes a progressive alteration in the nature of the skin and hair.

Because of the differences in the nature of the hair and skin, which can be major even between people in the same population group or even different individuals, individualized skin and hair care cannot be done with the care preparations available so far. In that case, to make this possible, many ready-to-use care preparations with different quantities of care preparation additives would have to be furnished, which is impracticable.

Many demands are made of hair care preparations. They should improve the manageability, feel, elasticity, sheen and volume while at the same time burdening the hair as little as possible. The term "burdening the hair" is understood to be the deposit of substances on the hair that is perceptible to and can be felt by the user of a hair treatment preparation and that makes the user feel her hair is not clean. The care preparations up to now cannot provide satisfaction in terms of meeting the demands for an individualized treatment effect, so there is an unmet need in this respect.

So far, it has been possible to improve negative hair conditions using conventional hair therapy preparations. Hair therapy preparations with a treatment effect and that improve manageability are therefore of major importance in modern hair care. Hair therapy preparations are typically in the form of emulsions or suspensions, which include monoalcohols or fatty alcohols, waxes, oils, or lipids; anionic, amphoteric, nonionic or cationic surfactants or emulsifiers. Emulsifiers, especially cationic emulsifiers, contribute substantially to the treatment effect.

However, a disadvantage of such hair care preparations is that the treatment effect is closely related to the emulsion properties. This means that there are narrow limits to the quantity of cationic surfactants to be used as care preparations. With a high concentration, advantageous emulsion properties would indeed be attainable, but would engender deleterious effects on the skin and hair. Especially with undamaged hair, an excessively strong treatment effect can ensue, which expresses itself in severe burdening of the hair, both when wet and when dry. If the treatment is too strong, the reverse effect on the hair can even ensue, where after the treatment, the hair is dull and even harder to comb than before.

Although lower concentrations of cationic surfactants cause no skin damage, they do not allow making usable emulsions, either, and provide only an unsatisfying treatment effect.

In the known hair care preparations, the treatment effect can accordingly be established only inadequately, because otherwise such emulsion properties as stability, viscosity and a creamy feel would be adversely affected.

Furthermore, cationic emulsifiers have the additional disadvantages that they irritate mucous membranes and are either not biodegradable or only poorly biodegradable.

Besides hair care preparations with cationic emulsifiers, those in the form of anionic hair care emulsions are also known. However, these hair care preparations have the disadvantage of an inadequate treatment effect, which cannot be improved substantially by further additions of amphoteric or nonionic surfactants, for instance.

In European Patent 0 662 816, for instance, a hair care preparation is described that includes cationic, amphoteric and nonionic polymers, alkylpolyglycosides and fatty alcohols and is intended for use in cleaning and caring for human hair.

Conventional cosmetic preparations can also be found in Chemical Abstracts 119-55722t or are described in European Patent Disclosures EP-A 0 728 460, EP-A 0 719 539, EP-A 0 705 593, and EP-A 0 641 557, and U. S. Pat. Nos. 5,118,507 and 5,250,289. In these and other cases, conditioners and vehicle substances are present together in mixture form. Such cosmetic care preparations, however, are not suited to attaining the object of the present invention.

SUMMARY OF THE INVENTION

It is therefore the object of the present invention to make a cosmetic care preparation available which does not have the disadvantages of the prior art and which meets the need for individualized care adapted to the particular skin and/or hair quality and the particular skin and/or hair type.

This object is attained, in part, by providing a cosmetic care preparation according to the invention, which is in the form of a two-component preparation, wherein the first component includes at least one conditioner and the second component substantially includes typical non-conditioning cosmetic vehicle substances, and in which the first and the second component, as precursor products, are separate until use and are not present in mixed form until in the final, ready-to-use product.

A preferred cosmetic care preparation according to the invention is comprised in that the care preparation is an apportionable cosmetic care preparation, in which the first and the second component, as precursor products, are separate until use and are not present in mixed form, in variable, selectable, or adjustable quantities, until in the final, ready-to-use product.

The term "at least one conditioner" is understood to mean that the first component includes one or more conditioners, which can be present either together in mixture form or each separately from one another, but in any case are spatially separate from the substantially non-conditioning second component until the actual care preparation ready for use (the final product) is made.

A decisive aspect of the care preparation of the invention is that the second component by itself exerts no treatment effect, or only an insignificant treatment effect, and the actual treatment effect in the ready-to-use product is brought about by the first component, which is variable and selectable in its quantity. In this sense the second component serves essentially as a vehicle or as a cosmetic foundation for the conditioners contained in the first component.

As with the need for individualized hair care, the same is true for the skin, since a hair care preparation, properly used, necessarily also comes into contact with the skin of the scalp. Yet the skin, too, depending on its individual nature, also requires individualized care. It is accordingly clear to one skilled in the art that the cosmetic care preparation of the invention can advantageously used generally in the field of cosmetic care; it does not matter whether the care is directed to the skin, or to the hair that grows out of the skin.

With the care preparation of the invention it is thus advantageously possible to adapt hair or skin care to the various needs that arise from different hair and skin quality and individual hair and skin type. With the care preparation of the invention, a treatment effect can thus be adjusted individually, that is, custom-tailored, with one and the same product by the apportioned use of preparations with a hair-care and/or skin-care effect.

By means of the separation according to the invention of care-type ingredients and vehicle substances and the apportioned addition of the care preparation, contained in the first component, to the final, ready-to-use product only immediately before the intended use, a gentle treatment effect on the skin and on the hair (of the scalp or the beard) that grows from the skin is achieved. It is understood that gentle treatment of the scalp hair or the hair of the face can also be attained when the care preparation of the invention is used as a hair care preparation.

When the preparation of the invention is used as a hair care preparation, the manageability, feel, elasticity, sheen and volume of the hair are improved, while burdening of the hair is markedly reduced; the two-component application according to the invention has the particular advantage that by the variability of the quantity of individual components, it is possible to adapt the hair treatment to special, individual hair qualities or to particular kinds of hair damage. Hair that is less severely damaged, for instance, does not need as much of the conditioners as more severely damaged hair. The consumption of raw materials can accordingly be reduced as well.

An additional advantage of the cosmetic care preparation of the invention resides in its chemical and/or physical stability, both with regard to the material composition that can be used and with regard to the usable concentrations of compositions of the first and second component. Examples of this would be stabilities of the pH value or of emulsions, both during storage and when the ready-to-use product is used. Conventional preparations have the disadvantages that compositions and concentrations of adjuvants, vehicle substances and care preparations in mixture form often have chemical and/or physical instabilities.

The cosmetic care preparation of the invention can therefore be used advantageously for caring for the hair and skin, and thus the use of the care preparation of the invention to suit a particular purpose is also encompassed by the present invention.

Cosmetic vehicle substances or foundation substances are understood according to the invention to mean all substances, compounds or mixtures known to one skilled in the art that by themselves develop no cosmetic treatment effects, or only insignificant treatment effects.

In principle, one skilled in the art knows which vehicle substances and foundation substances and which conditioners are used in hair and skin cosmetics, and so the further descriptions below are merely in the nature of examples and are intended to illustrate the present invention.

The available literature may also be referred to, for instance K. Schrader, *Grundlagen und Rezepturen der Kosmetika* [Fundamentals and Formulas in Cosmetics], 2nd edition, 1989, pages 728–737, or A. Domsch, *Die kosmetischen Präparate* [Cosmetic Preparations], Verlag für chemische Industrie (H. Ziolkowsky, Ed.), 4th edition, Vol. 2, pages 212–230, 1992.

What is preferred according to the invention is a cosmetic two-component care preparation, which is in the form of a hair care preparation. The description below will in this sense use the term hair care preparation, but without limiting the present invention to this subject only. One skilled in the art is familiar with which conditioners, additives, containers or equipment are usable for which purpose (skin care preparation or hair care preparation).

With regard to the first component, which according to the invention is intended to develop the actual caring effect, it contains one or more care preparations, known in cosmetics, of the most various classes of compounds and substances. Included in particular here are anionic, cationic, amphoteric or nonionic surfactants and/or polymers, oils, fats, and/or waxes or derivatives (such as alcohols, esters, silicone compounds) thereof.

The conditioners may be present individually or in mixture form. For instance as mixtures of various cationic surfactants or as mixtures of various cationic polymers or as a surfactant and polymer mixture, or as mixtures of oils, fats, waxes and derivatives thereof, or as mixtures of two or more of these substances.

Among the care preparations of the first component, cationic care preparations are preferred, especially if they include surfactants and polymers.

Suitable cationic surfactants and polymers include fatty amines; quaternary ammonium compounds; quaternary compounds of pyridine, morpholine or imidazoline, or a mixture thereof; as well as cationic copolymers, cationic mixed polymers, cationic polysaccharides, cationic cellulose derivatives, cationic or cationized hydrolyzed proteins such as collagen or keratin, or a mixture thereof.

The following examples of cationic surfactants can be named: Genamin® CTAC or cetyltrimethylammonium chloride (THA chloride) (Hoechst, Germany); quaternary esters, such as tetradecylbetaine ester chloride; diquaternary esters, such as dipalmitoylethyldimethylammonium chloride (Armocare VGH70 made by Akzo, Germany); or a mixture of distearoylethyl hydroxyethylmonium methosulfate and cetearyl alcohol (Dehyquart F-75 made by Henkel, Germany); diquaternary silicones, such as Abil Quat 3272 (Quaternium-80 made by Th. Goldschmidt A G, Germany); or imidazolidinyl derivatives, such as Rewoquat W 575 (Quaternium-87 made by Witco, Germany).

Examples of cationic polymers that can be named are Luviquat® FC 905 (copolymer of vinylimidazolium methochloride and vinyl pyrrolidone, or Polyquaternium-16) made by BASF, Germany, or Gafquat® 755 N (copolymer of vinyl pyrrolidone and dimethylaminoethylmethacrylate, or Polyquaternium-11) made by ISP, New Jersey, USA, or UcarePolymer JR400 (Polyquaternium-10) made by Amerchol, New Jersey, USA, or Merquat 550 (Polyquaternium-7) made by Chemviron, or Cosmedia Guar C 261 (hydroxypropyl guar hydroxypropyltrimonium chloride) from Henkel, Germany, or Jaguar C13S (guar hydroxypropyltrimonium chloride) made by Rhône-Poulenc, France, or Lamequat L (lauryldimonium hydroxypropyl hydrolyzed collagen) made by Henkel, or Gluadin WQ (lauryldimonium hydroxypropyl hydrolyzed wheat protein) from Henkel, or Celquat L-200 (Polyquaternium-4) made by National Starch, New Jersey, USA.

Cationic conditioners, especially if they are surfactants, can be present in the first component in a quantity of between 0.1 and 50.0 weight %. In the case of cationic polymers, they can preferably be contained in a quantity of between 0.1 and 30.0 weight %. For the total amount of cationic conditioners, whether they are surfactants or polymers, a preferred range of between 1.0 and 20.0 weight % can be given.

For example, a first component as a care preparation can comprise a mixture including at least one vegetable oil and tocopherol acetate, which is dissolved in volatile silicone oil. Other examples would be: a solution of cetyltrimethylammonium chloride and a cationic polymer, which may further contain a solution of strengthening polymers for increasing the volume of the hair, and/or an anti-dandruff agent (such as climbazole or zinc pyrithion) and/or a moisturizer (such as a solution of pantothenol or hyaluronic acid in water and/or glycerin), and/or neutralizers (such as a solution of glyoxylic acid in water for neutralizing oxidants that have not been rinsed out).

A further example for an advantageous embodiment of the first component is that it substantially comprises a hydrophobic composition of one or more hair- and/or skin-care fats, oils or waxes, individually or in mixture form. Examples of such conditioners are silicone oils (such as cyclomethicones, like Dow Corning 345 Fluid, dimethicones such as Dow Corning 200 Fluid, amino-functional silicones such as SM 2115-D2 made by GE Silicones, silicone gums such as Toshiba XF49-811); triglycerides, such as avocado oil; fatty acids, fatty alcohols, easy-spreading oils such as isopropyl myristate, Cetiol OE (dicaprylyl ether) or Eutanol G (octyldodecanol), obtainable from Henkel, Germany; waxes, such as lanolin, apple wax, ilex resin, beeswax or jojoba oil; phospholipids such as lecithin; or ceramides; or petroleum fractions, such as paraffin oils and paraffin waxes, or vaseline.

Along with silicone oils, the first component can also contain, as a care preparation, fatty acid esters, fatty alcohol ethers or fatty alcohol esters, for instance in a quantity of 0.1 to 10 weight %. These compounds are derived from fatty acids or fatty alcohols that have a straight or branched carbon chain with from 6 to 40 carbon atoms, are saturated or unsaturated, and can also contain OH groups in the chain. Branched compounds occur both in synthetic esters and ethers and in natural waxes. Unsaturated and hydroxylated fatty acids and fatty alcohols occur in triglycerides and waxes. Suitable compounds are for instance wheat germ oil, sperm oil, derivatives of lanolin alcohol and of lanolinic acid, octyl stearate (Cetiol® 868 from Henkel), hexyl laurate Cetiol® A from Henkel), dioctyl adipate (Arlamol® DOA made by ICI), isopropyl myristate, and octyldodecanol (Eutanol® G from Henkel), spermaceti, beeswax, and fruit waxes and other vegetable waxes.

In the hair care preparation of the invention, silicone oils can also be added to these fatty acid esters, fatty alcohol ethers or fatty alcohol esters.

In a further exemplary embodiment, the first component can comprise at least one saturated or unsaturated fatty acid glyceride, for instance in a quantity of from 0.6 to 40 weight %, and/or at least one ester formed from a saturated or unsaturated fatty acid and a saturated or unsaturated fatty alcohol, for instance in a quantity of from 0.3 to 20 weight %, and/or at least one silicone compound, preferably a volatile silicone compound, for instance in a quantity of from 0.3 to 20 weight %. A combination of these conditioners is preferred.

For instance, the fatty acids (fatty acid glyceride and esters) can preferably be predominantly unsaturated and can preferably have a chain length of from 12 to 30 carbon atoms, and especially preferably of from 16 to 22 carbon atoms. The quantitative ratio of fatty acid glycerides to the esters can preferably range from approximately 1:2 to approximately 10:1, and especially preferably from approximately 1:1 to approximately 6:1.

The fatty acids and esters may be of synthetic or natural origin, preferably natural.

The fatty acid glycerides can be present in mixture form. A suitable and preferred mixture of fatty acid glycerides of natural origin is for example avocado oil or sunflower oil. Sunflower oil substantially comprises a mixture of fatty acid glycerides, in which the following fatty acids are contained: 4 to 9% palmitic acid, approximately 1% palmitoleic acid, 1 to 7% stearic acid, 15 to 35% oleic acid, 50 to 72% linoleic acid, approximately 2% linolenic acid, approximately 1% icosanoic acid, and approximately 2% docosanoic acid. Avocado oil substantially comprises a mixture of fatty acid glycerides, in which the following fatty acids are contained: 5 to 25% palmitic acid, 1 to 10% palmitoleic acid, approximately 3% stearic acid, 54 to 74% oleic acid, 6 to 16% linoleic acid, and approximately 3% linolenic acid. Also suitable are other oils, especially natural oils, which substantially comprise unsaturated fatty acids such as mink oil, olive oil, almond oil, palm oil, peanut oil, cottonseed oil, rapeseed oil, safflower oil, or grapeseed oil.

These esters, formed form a saturated or unsaturated fatty acid and a saturated or unsaturated fatty alcohol, cal so be present in mixture form. A suitable mixture of esters of natural origin formed from fatty acid and fatty alcohol is jojoba oil, for example. Jojoba oil substantially comprises a mixture of esters formed from fatty acids and the corresponding fatty alcohols, in which the following fatty acids are contained: approximately 1 to 2% palmitic acid, approximately 10% stearic acid, approximately 71% icosanoic acid, and approximately 13 to 14% docosenoic acid.

In general, all known products can be used as silicone compounds or silicone oils for the first, care-type component. Suitable examples are thin-bodied silicone oils, hexamethyldisiloxane, polydimethylsiloxane (INCI: dimethicones), preferably with up to 8 monomer units, cyclic dimethylpolysiloxane (INCI: cyclomethicones), such as cyclooctamethyltetrasiloxane, cyclodecamethylpentasiloxane (such as Dow Corning 244 Fluid or Dow Corning 200 Fluid), phenyltrimethicones (such as Abil AV types made by Goldschmidt), dimethiconol (such as Dow Corning 1401), alkyldimethicones (such as Dow Corning 2502 and 2503) or amino-functional silicones (such as Dow Corning 939 or 8220), where the silicone compounds can preferably have a viscosity of below 100 mm$^2$/s, and especially preferably below 20 mm$^2$/s. Mixtures of silicone compounds or silicone oils are also suitable.

The silicone compounds or silicone oils can be used in concentrations of from 0.02 to 20 weight %.

A preferred cosmetic care preparation according to the present invention is comprised in that the first component comprises a combination composed of at least one saturated or unsaturated fatty acid glyceride, at least one ester formed from a saturated or unsaturated fatty acid and a saturated or unsaturated fatty alcohol, and at least one silicone compound.

It is understood that conditioners other than those named may be contained in the first component, either individually or in mixture form, including in mixtures with those named. Examples would be lanolin derivatives, cholesterol, betaines, carnitine esters, amino acids, peptides, proteins, vitamins, and mixtures thereof, for instance in a quantity of from 0.1 to 10.0 weight %. As proteins, keratin can be used, for instance, in a quantity of from 0.1 to 4.0 weight %. As amino acids, cysteine or alanine can be named, in a quantity of from 0.01 to 0.5 weight %.

Like the other conditioners in the first component, these may be present individually, or in a mixture either separately from one another or together.

The second component with the substantially non-conditioning effect can comprise cosmetic foundations or adjuvants and vehicle substances, of the kind typically used in cosmetic preparations. Accordingly, the second component includes at least one preparation usable for cosmetic purposes, with emulsifying or self-emulsifying and/or consistency-providing properties. Such a preparation can for instance be in the form of a emulsion or an ingredient of an emulsion or base emulsion.

All thin-bodied aqueous and alcoholic, fatty, oily, waxlike, polymeric, viscous vehicle substances are suitable for this. Examples that can be listed are water, alcohols (such as ethyl alcohol, propyl alcohol, isopropyl alcohol), fatty alcohols, viscous substances or thickeners, such as cellulose derivatives (for instance, hydroxyethyl cellulose, hydroxypropyl cellulose), or aluminum silicates, protein derivatives (such as hydrolyzed collagen), surfactants, polymers, and emulsifiers, in each case either individually or in mixture form.

Preferably, the second component includes an amphoteric surfactant, a nonionic surfactant, an anionic surfactant, a cationic base emulsion, or an anionic base emulsion.

As surfactants, amphoteric and/or nonionic surfactants are preferably possible, if the second component for instance is intended to be in the form of an emulsion. Anionic surfactants may be preferably used, if a shampoo is to be formulated as the ready-to-use product. In principle, however, one skilled in the art will be familiar with which surfactants are used for which purpose.

With regard to the amphoteric surfactants, all known amphoteric surfactants known in cosmetic products are possible for the second component. In particular, those selected from the group comprising betaines, sulfobetaines, glycinates, acetates or propionates, including their salts of addition. Of these, above all the N-alkylbetaines, N-alkylaminobetaines, N-alkylsulfobetaines, N-alkylaminopropionates, alkyldimethylammonium acetates and fatty acid alkylamidobetaines can be named as suitable amphoteric surfactants for component A. Those that are quite particularly preferred, however, are cocamidopropylbetaine, cocoamphodipropionate, lauroamphocarboxyglycinate, or cocoamphoacetate, including their salts of addition, such as sodium cocoamphoacetate. Naturally, the amphoteric surfactants named may be present in the second component individually or in mixture form.

Amphoteric surfactants are known from the prior art and are available commercially, such as Miranol Ultra CLS from Rhône-Poulenc.

As nonionic surfactants, once again all the nonionic surfactants known to be used in cosmetic preparations can be considered for the second component. Examples that can be used are ethoxylated fatty alcohols (such as the Eumulgin types made by Henkel) or fatty acid glycerides with from 12 to 18 carbon atoms and up to 40 mol of ethylene oxide per mol of fatty alcohol, such as ethoxylated lauryl alcohol, tetradecyl alcohol, cetyl alcohol, oleyl alcohol, or stearyl alcohol, either alone or in mixture form; and fatty alcohols of ethoxylated lanolin, or ethoxylated lanolin. However, fatty amine ethoxylates, fatty acid alkanolamides, sugar esters (such as saccharose esters, for example the Ryoto types made by Syntapharm) and sugar ethers (such as alkylpolyglucosides, for instance the Plantacare types made by Henkel), polyglyceryl esters, silicone surfactants (such as alkoxylated polysiloxanes, such as Dow Corning Surfactant 193 or Dow Corning 5324 Fluid, or silicone-sugar copolymers, such as Wacker SPG 128) and ethoxylated sorbitane fatty acid esters are also suitable as nonionic surfactants or surfactant mixtures.

Anionic surfactants can also be used in the usual scope in cosmetics, such as alkali, alkaline earth, ammonium or alkanolamine salts of alkane sulfonates, alkyl sulfates and alkyl ether sulfates, which contain from 12 to 18 carbon atoms in the alkyl radical, and in particular the sodium or triethanolamine salts of lauryl or tetradecyl ether sulfates.

The known surfactants and polymers of mixtures thereof that are suitable for the second component may be present in a quantity between 0.1 and 30.0 weight %, and preferably in a quantity between 0.5 and 20.0 weight %.

Particularly for hair care, it may be advantageous if the second component contains at least one preparation with emulsifying or self-emulsifying, consistency-lending properties. Possible examples for this are all known ionic emulsifiers (with carboxylic acid, sulfonic acid, or sulfuric acid groups), amphoteric emulsifiers (with basic or acidic hydrophilic groups) or nonionic emulsifiers (such as polyglycol ethers, fatty acid esters such as glycol fatty acid esters, glycerin monofatty acid esters or sorbitane fatty acid esters), or at least one monoalcohol (or fatty alcohol). With regard to monoalcohols, monovalent, saturated or unsaturated, linear or branched alcohols with from 6 to 30 carbon atoms, preferably 12 to 22 carbon atoms, or a mixture thereof, are possible. Examples of fatty alcohols are octanol, decanol, dodecanol or lauryl alcohol, tetradecanol or myristyl alcohol, hexadecanol or cetyl alcohol, octadecanol or stearyl alcohol, or mixtures of these fatty alcohols, such as a mixture of cetyl alcohol and stearyl alcohol (cetearyl alcohol).

Monoalcohols that can be considered according to the invention are known from the prior art and are commercially available, for instance from Henkel in Düsseldorf, Germany.

The monoalcohols or a mixture of them can be present in a quantity of between 0.1 and 20.0 weight %, and preferably in a quantity of between 0.5 and 10.0 weight %.

Suitable consistency lenders and thickeners may be agar-agar, guar gum, alginates and xanthan gum, or esters of ethoxylated polyols and fatty acids, such as polyglyceryl(2) polyoxyethylene(4) stearate.

In another preferred version, the care preparation of the invention is comprised in that the base emulsion of the second component is a cationic or anionic base emulsion.

According to the invention the term cationic base emulsion is understood to mean an emulsion which along with water and a lipophilic ingredient includes at least one cationic emulsifier. An anionic base emulsion is understood to mean an emulsion which along with water and a lipophilic ingredient includes at least one anionic emulsifier.

A suitable cationic base emulsion can for instance contain a combination of at least one lipophilic substance, preferably in a quantity of from 3 to 10 weight %; at least one cationic emulsifier, preferably in a quantity of from 1 to 3 weight %; an organic acid in a quantity of from 0 to 3 and preferably 0.1 to 3 weight %; and water, preferably in a quantity of from 60 to 90 weight %.

A suitable anionic base emulsion can for instance contain a combination of at least one lipophilic substance, preferably in a quantity of from 3 to 10 weight %; at least one anionic emulsifier, preferably in a quantity of from 1 to 3 weight %; an organic acid in a quantity of from 0 to 3 and preferably 0.1 to 3 weight %; and water, preferably in a quantity of from 60 to 90 weight %.

Suitable lipophilic substances are for instance fatty alcohols, vaseline or paraffin oils, of which fatty alcohols are preferred. Preferred fatty alcohols are linear and have a chain length of from 8 to 22 carbon atoms.

Preferred cationic emulsifiers are alkyltrimethylammonium halides or dialkylmethylammonium halides, in which the alkyl group comprises 8 to 18 carbon atoms.

Preferred anionic emulsifiers are for instance salts of fatty acids, fatty alcohol or alkyl sulfates, sulfonates or phosphates, in which the alkyl group comprises from 8 to 18 carbon atoms.

Suitable organic acids are for instance formic acid, glyoxylic acid, lactic acid, tartaric acid or citric acid; citric acid is especially preferred.

What is preferred is an apportionable cosmetic care preparation which is characterized in that the first component is composed of at least one cationic surfactant and/or at least one cationic polymer, and the second component is composed of at least one preparation with emulsifying or self-emulsifying and/or consistency-lending properties.

What is quite particularly preferred is an apportionable cosmetic care preparation which is characterized in that the first component is composed of at least one cationic surfactant and/or at least one cationic polymer, and the second component is composed of at least one monoalcohol and/or at least one amphoteric or nonionic surfactant.

An also-preferred embodiment of the invention resides in a cosmetic care preparation, which is characterized in that the first component comprises a combination composed of at least one saturated or unsaturated fatty acid glyceride, at least one ester formed from a saturated or unsaturated fatty acid and a saturated or unsaturated fatty alcohol, and at least one silicone compound, and that the second component comprises a cationic or anionic base emulsion.

Other known cosmetic additives, adjuvants and vehicle substances can be added to the care preparation of the invention, examples being solvents, such as lower aliphatic alcohols with from 1 to 4 carbon atoms, such as ethanol isopropanol or propanol, or glycols such as glycerin or 1,2-propylene glycol. The solvents are preferably in a quantity of from 0.5 to 90 weight %. The following can also be included: perfume oils in a quantity of from 0.1 to 5 weight %; opacifiers such as ethylene glycol distearate in a quantity of from 0.2 to 5 weight %; wetting agents or emulsifiers selected from the classes of anionic, cationic, amphoteric or nonionic surfactants, such as fatty alcohol sulfates, alkyl benzene sulfonates, alkyltrimethylammonium salt,; alkyl betaines, ethoxylated fatty alcohols, ethoxylated nonyl phenols, ethoxylated fatty acid esters in a quantity of from 0.1 to 30 weight %; as well as bactericidal and fungicidal ingredients; thickeners (such a bentonite); pH buffer substances; moisture retaining agents; fragrances or perfumes; perfume oils; colorants (such as natural or synthetic direct dyes but also tinting agents such as fluorescein sodium salt); sunscreens or UV filters; preservatives; antioxidants (such as tocopherols); pyrogenic silicic acid; complexing agents; anti-dandruff ingredients; and also physiologically tolerable inorganic or organic acids, such as phosphoric acid, acetic acid, formic acid, glyoxylic acid, lactic acid, tartaric acid or citric acid; bases; salts (such as sodium chloride); buffers (such as sodium citrate or sodium phosphate); consistency-lending agents; and natural, modified, partly or entirely synthetic polymers (such as chitosan, FMOC chitosan, and PVP).

As the additives, adjuvants and vehicle substances, the following examples can also be named: preservatives, such as parahydroxybenzoic acid esters in a quantity of from 0.05 to 2.0 weight %; fungicidal and bactericidal ingredients, such as 2,4,4-trichloro-2-hydroxyphenyl ether or methyl-chloroisothiazolinone; plant extracts, such as stinging nettle extract or chamomile extract in a quantity of from 0.1 to 2.0 weight %; sunscreens or UV filters, such as p-methoxycinnamic acid isoamyl ester, lipophilic cinnamic acid esters, salicylic acid esters, 4-aminobenzoic acid derivatives, or the hydrophilic sulfonic acid derivatives of benzophenones or of 3-benzylidene camphor in a quantity of from 0.01 to 2.0 weight %; and thickeners, such as cellulose and esters thereof in a quantity of from 0.5 to 3.0 weight %. As vitamins, vitamin C in a quantity of from 0.1 to 2.0 weight % can be considered. As antioxidants, tocopherols in a quantity of from 0.001 to 5.0 weight % can for instance be used. As emulsifiers, in particular nonionic emulsifiers can be used, such as Plantacare or alkyloligoglucoside from Henkel, Düsseldorf, Germany, in a quantity of from 0.1 to 2.0 weight %. As solubilizers, Cremophor RH 410 or glycerin polyethylene glycol hydroxystearate from BASF, Ludwigshafen, Germany, in a quantity of from 0.1 to 2.0 weight % are for instance possible.

Naturally one skilled in the art will be familiar with which of the various individual adjuvants and vehicle substances he will have to add in order to obtain a desired formulation of the care preparation of the invention. For instance, for skin care in the form of a creme, paste, gel, milk or lotion, he will select the fats, oils, waxes, emulsifiers, thickeners or perfumes suitable for the purpose. For a hair care preparation of the present invention, once again one skilled in the art will need not expend any effort in using the appropriate surfactants, polymers, emulsifiers, or perfumes.

As colorants, all the known physiologically tolerable colorants are possible. These colorants can have the function of acting as an indicator for the intensity of the desired treatment effect or for the quantity of care preparation contained in the first component and can act as an apportioning control. In that case, such a colorant is added to the first component. For that purpose, colorants that can be considered are those which preferably have no dyeing effect on the hair or skin, such as fluorescein sodium salt. Such a color indicator is an advantageous possibility when a gel, foam, paste or creme or other formulation that has a consistency suitable for the purpose is used. Such a color indicator can advantageously be introduced together with the first component into solid or deformable containers (tubes, cans, bottles) equipped with two chambers.

However, colorants can also be added to the care preparation of the invention whenever the care preparation also contains a hair dye and which have a permanent hair-dyeing property. All the known dyes for this purpose can be considered.

Such colorants may for instance be the known nitro dyes, selected from the group comprising nitro- and amino- substituted benzenes, benzonitriles or benzamides. However, the known azo dyes or quinone dyes, as well as such natural dyes as henna, indigo or juglone can also be considered.

The first and second component can be mixed in any ratio suitable for the intended purpose and the desired treatment effect. A ratio of the first component to the second component in the range from 20:1 to 1:20 in the product ready for use is preferred.

In general, it can be assumed that for using the care preparation of the invention, the two components will be mixed within 10 minutes, preferably within 2 minutes, and in particular within 1 minute prior to use.

For the case where the care preparation of the invention is used as a hair care preparation in the form of a rinse, it can be rinsed out with water after being left on the hair to act for between 1 and 30 minutes, preferably between 2 and 20 minutes, and in particular between 2 and 10 minutes.

For the case where the intended use is as a hair care preparation, the action time can be permanent, and can last for hours or days without being rinsed out afterward.

The pH value of the two components and of the final ready-to-use product can range between 2.0 and 7.0, preferably between 3.0 and 6.0. If desired, to set a physiologically tolerable pH value, a suitable acid can be used. Adding citric acid, tartaric acid, lactic acid, adipic acid, glyoxylic acid, gluconic acid and malic acid is suitable, but so is adding an inorganic acid, such as phosphoric acid.

The ready-to-use product, that is, the first and second component mixed apportionably together immediately prior to use, can include all types of application known to one skilled in the art and desired by the user. Depending on the type of application, the ready-to-use care preparation can be thin-bodied (for instance so it can be sprayed on), or viscous to creamy or pasty (so it can be applied with the hands, for instance).

If it is intended for use as a hair care preparation, the care preparation of the invention can advantageously be in the form of an oil-in-water emulsion, which can also be sprayed on as an aerosol or as a foam with the aid of a pump.

As suitable formulations, all the conventional formulations and forms of administration known in cosmetics as used for skin and hair care preparations can be used. Possible examples are for instance emulsions, foams, gels, cremes, pastes, aqueous or alcoholic or aqueous-alcoholic solutions, lotions or suspensions (for instance with bentonite or other particles). The ready-to-use care preparation can for instance be in the form of a shampoo, rinse, hair tonic, lotion, gel, foam or gel foam (mousse), or in sprayable form (spray).

The second component for formulations of a suitable care preparation (such as emulsions, gels, pastes, sprays or foams) can be prepared in the usual way for one skilled in the art. The ingredients for the first component can likewise be prepared or mixed by methods known per se, such as simply being stirred with heat.

These preparation forms can be dispensed into and kept on hand in all the usual solid or deformable containers for comparable cosmetic products (such as cans, bottles, tubes, or spray cans with a propellant or that use a mechanically operated sprayer), as long as these containers have two-chamber systems or two separate containers that make it possible to keep the first and second component spatially separate and to combine them only immediately before use, and that allow a variable, that is, apportionable, admixture of the first component to the second component, or vice versa. Devices suitable for this purpose are known from the prior art, such as from European Patent EP 0 335 763 or German Patent DE 2141436.

Accordingly, the present invention also encompasses a packaging unit including a care preparation of the invention, which is characterized in that in it, the first component and the second component are contained spatially separately from one another, and that the first component can be mixed apportionably with the second component in variable, selectable or adjustable quantities immediately before use.

It also encompasses a packaging unit in which the suitable additives, spatially separate from a first and second component, are present as a third component. This third component can advantageously include further conditioners. Such an arrangement has the advantage that mixtures, which are not stable in storage, of additives, such as conditioners, are present in stable form as separate precursor products and can be used in the final product, advantageously in apportionable fashion.

The invention also encompasses a method for care of the skin and hair which is characterized in that a first component including at least one care preparation and a second, substantially non-conditioning component are mixed immediately before use, and the first component is added to the second component in variable, selectable, or adjustable quantities. The ratio of the first component to the second component can range, after the mixing, from 20:1 to 1:20.

The subject of the present invention is also a method for producing the apportionable cosmetic care preparation of the invention. This method is characterized in that the first component and the second component are prepared separately in a manner known per se and poured into a container in such a way that the two components are present spatially separately from one another, and that the first component can be mixed apportionably in variable, selectable and adjustable quantities with the second component immediately before use to make the finished final product.

The following examples are intended to describe the subject of the invention in further detail, but without limiting it to them. The oil complexes 1–5 of Examples 1–5 pertain to ingredients in the first component, while Examples 6–9 pertain to the usual cosmetic base emulsions present as the second component. Example 10 a further second, non-conditioning component.

EXAMPLE 1

Oil Complex 1

| | |
|---|---|
| 18.0 g | jojoba oil |
| 15.0 g | avocado oil |
| 15.0 g | sunflower oil |
| 52.0 g | cyclic polydimethylsiloxane (DOW Corning 244 made by Dow Corning Europe, in Belgium) |
| 100.0 g | |

EXAMPLE 2

Oil Complex 2

| | |
|---|---|
| 8.0 g | jojoba oil |
| 20.0 g | avocado oil |
| 21.0 g | sunflower oil |
| 51.0 g | cyclic polydimethylsiloxane (Dow Corning 244 made by Dow Corning Europe, in Belgium) |
| 100.0 g | |

EXAMPLE 3

Oil Complex 3

| | |
|---|---|
| 22.0 g | jojoba oil |
| 19.0 g | avocado oil |
| 18.0 g | sunflower oil |
| 50.0 g | cyclic polydimethylsiloxane (DOW Corning 244 made by Dow Corning Europe, in Belgium) |
| 100.0 g | |

EXAMPLE 4

Oil Complex 4

| | |
|---|---|
| 16.0 g | jojoba oil |
| 17.0 g | avocado oil |
| 13.0 g | sunflower oil |
| 54.0 g | cyclic polydimethylsiloxane (Dow Corning 244 made by Dow Corning Europe, in Belgium) |
| 100.0 g | |

EXAMPLE 5

Oil Complex 5

| | |
|---|---|
| 1.3 g | jojoba oil |
| 1.5 g | avocado oil |
| 1.3 g | sunflower oil |
| 95.9 g | cyclic polydimethylsiloxane (Dow Corning 244 made by Dow Corning Europe, in Belgium) |
| 100.0 g | |

EXAMPLE 6

Cationic Base Emulsion for a Two-component Preparation

| | |
|---|---|
| 3.5 g | cetyl stearyl alcohol |
| 0.9 g | cetyltrimethylammonium chloride |
| 0.4 g | citric acid |
| 0.4 g | perfume oil |
| 94.8 g | water |
| 100.0 g | |

EXAMPLE 7

Cationic Base Emulsion for a Two-component Preparation

| | |
|---|---|
| 7.0 g | cetyl stearyl alcohol |
| 2.1 g | cetyltrimethylammonium chloride |
| 2.1 g | lanolin |
| 0.5 g | perfume oil |
| 88.3 g | water |
| 100.0 g | |

EXAMPLE 8

Anionic Base Emulsion for a Two-component Preparation

| | |
|---|---|
| 2.5 g | cetyl stearyl alcohol |
| 0.8 g | lauryl alcohol diglycol ether |
| 1.1 g | vaseline |
| 0.4 g | cetyl stearyl sulfate, sodium salt |
| 5.0 g | betaine monohydrate |
| 0.2 g | benzoic acid ester |
| 0.8 g | glyoxylic acid |
| 0.3 g | perfume oil |
| 88.9 g | water |
| 100.0 g | |

EXAMPLE 9

Anionic Base Emulsion for a Two-component Preparation

| | |
|---|---|
| 4.4 g | cetyl stearyl alcohol |
| 1.0 g | cetyl stearyl sulfate, sodium salt |
| 1.6 g | glycerin monodistearate / potassium or sodium stearate (Tegin$^R$ made by Goldschmidt, Germany) |
| 2.1 g | lanolin |
| 0.1 g | petrolatum |
| 0.1 g | mineral oil |
| 0.1 g | cholesterol |
| 2.3 g | lanolin alcohol |
| 0.3 g | propyl-p-hydroxybenzoate |
| 0.4 g | perfume oil |
| 87.6 g | water |
| 100.0 g | |

Before use, from 20 to 30 ml of the base emulsion of one of Examples 6–9 is mixed with from 2 to 8 ml of an oil complex of Examples 1–5.

After that, the preparation is employed as usual: The hair is washed, and the preparation of the invention is distributed carefully through the hair. After an action time of 15 to 30 minutes, the preparation is rinsed out with water.

EXAMPLE 10

Nonionic, Non-conditioning Component A for Cremes and Lotions

| | |
|---|---|
| Cetearyl alcohol (Lanette O) | 5.5 weight % |
| Glyceryl stearate SE (Tegin) | 2.5 weight % |
| Lauryl polyglucose (Plantaren 2000) | 1.5 weight % |
| p-Hydroxybenzoic acid methyl ester | 0.1 weight % |
| Perfume | 0.4 weight % |
| Water, fully desalinated, to make up | 100.0 weight % |

The preparation was done by methods known per se: The solution of water-soluble raw materials, heated to 80° C., was stirred into the wax phase that is molten at 80° C. The emulsion was left to emulsify for 5 minutes at 80° C., then optionally homogenized, and then cooled down, stirring occasionally. At 30° C., the perfume was worked in, and the losses of water from evaporation were made up for with fully desalinated water.

EXAMPLE 11
Hair Care Preparation in the Form of a Rinse for Only Slightly Damaged Hair, with an Amphoteric Vehicle

| First Component: | |
| --- | --- |
| Polyquaternium-11 | 10.0 weight % |
| Water, fully desalinated, to make up | 100.0 weight % |
| Second Component: | |
| Tetradecyl alcohol | 5.0 weight % |
| Sodium cocoamphoacetate | 4.0 weight % |
| Citric acid | 0.2 weight % |
| Perfume | 0.5 weight % |
| Water, fully desalinated, to make up | 100.0 weight % |

20.0 grams of the second component and 2.0 grams of the first component were mixed and then applied, after shampooing, to the towel-dried, only slightly damaged hair. After an action time of five minutes, the preparation was rinsed out. The hair had been given a well-groomed feel, without seeming burdened.

EXAMPLE 12
Hair Care Preparation in the Form of a Rinse for More Severely Damaged Hair, with an Amphoteric Vehicle

| First Component: | |
| --- | --- |
| Polyquaternium-10 | 5.0 weight % |
| Water, fully desalinated, to make up | 100.0 weight % |
| Second Component: | |
| Tetradecyl alcohol | 5.0 weight % |
| Sodium cocoamphoacetate | 4.0 weight % |
| Citric acid | 0.2 weight % |
| Perfume | 0.5 weight % |
| Water, fully desalinated, to make up | 100.0 weight % |

20.0 grams of the second component and 3.0 grams of the first component were mixed and then applied, after shampooing, to the towel-dried, more severely damaged hair. After an action time of five minutes, the preparation was rinsed out. The hair had been given a smooth feel, without seeming burdened.

EXAMPLE 13
Hair Care Preparation in the Form of a Rinse for Only Slightly Damaged Hair, with an Amphoteric Vehicle

| First Component: | |
| --- | --- |
| Cetyltrimethylammonium chloride | 10.0 weight % |
| Cetyl lactate | 2.0 weight % |
| Water, fully desalinated, to make up | 100.0 weight % |
| Second Component: | |
| Cetearyl alcohol | 4.0 weight % |
| Cocoamidopropyl betaine | 4.0 weight % |
| Citric acid | 0.1 weight % |
| Perfume | 0.3 weight % |
| Water, fully desalinated, to make up | 100.0 weight % |

20.0 grams of the second component A and 1.0 gram of the first component were mixed and then applied, after shampooing, to the towel-dried, only slightly damaged hair. After an action time of five minutes, the preparation was rinsed out. The hair had been given a well-groomed feel, without seeming burdened.

EXAMPLE 14
Hair Care Preparation in the Form of a Rinse for More Severely Damaged Hair, with an Amphoteric Vehicle

| First Component: | |
| --- | --- |
| Cetyltrimethylammonium chloride | 10.0 weight % |
| Cetyl lactate | 2.0 weight % |
| Water, fully desalinated, to make up | 100.0 weight % |
| Second Component: | |
| Cetearyl alcohol | 4.0 weight % |
| Cocoamidopropyl betaine | 4.0 weight % |
| Citric acid | 0.1 weight % |
| Perfume | 0.3 Weight % |
| Water, fully desalinated, to make up | 100.0 weight % |

20.0 grams of the second component and 2.0 grams of the first component were mixed and then applied, after shampooing, to the towel-dried, more severely damaged hair. After an action time of five minutes, the preparation was rinsed out. The hair had been given a smooth feel, without seeming burdened.

What is claimed is:

1. A two-component cosmetic care preparation consisting of a first component and a second component kept separate from the first component prior to application, wherein the first component and second component are not mixed to form a final, ready-to-use product until immediately prior to application;

wherein said first component includes at least one conditioner and the second component has emulsifying or self-emulsifying properties and/or consistency-providing properties and the second component comprises a cationic base emulsion or an anionic base emulsion;

wherein the cationic base emulsion includes at least one lipophilic substance, at least one cationic emulsifier, at least one organic acid and water; and wherein the anionic base emulsion includes at least one lipophilic substance, at least one anionic emulsifier at least one organic acid and water.

2. The cosmetic care preparation as defined in claim 1, wherein said at least one lipophilic ingredient is selected from the group consisting of fatty alcohols having from 8 to 22 carbon atoms, petrolatum and paraffin oils.

3. The cosmetic care preparation as defined in claim 1, wherein said at least one cationic emulsifier is selected from the group consisting of alkyltrimethyl ammonium halides and dialkylmethyl ammonium halides, wherein said alkyl groups of said halides contain from 8 to 18 carbon atoms.

4. The cosmetic care preparation as defined in claim 1, wherein said at least one anionic emulsifier is selected from the group consisting of fatty acid salts, fatty alcohol sulfates, alkyl sulfates, alkyl sulfonates and alkyl phosphates, wherein said alkyl groups of said sulfates, sulfonates and phosphates contain from 8 to 18 carbon atoms.

5. The cosmetic care preparation as defined in claim 1, wherein said at least one organic acid is selected from the group consisting of formic acid, glyoxylic acid, lactic acid, tartaric acid and citric acid.

6. The cosmetic care preparation as defined in claim 1, wherein said first component comprises a combination of at least one saturated or unsaturated fatty acid glyceride, at least one ester of a saturated or unsaturated fatty acid and a saturated or unsaturated fatty alcohol, and at least one silicone compound.

7. The cosmetic care preparation as defined in claim 1, wherein said first component includes at least one member selected from the group consisting of anionic surfactants, cationic surfactants, amphoteric surfactants, nonionic surfactants, polymers, oils, fats and waxes.

8. The cosmetic care preparation as defined in claim 1, wherein said first component includes a cationic surfactant and/or a cationic polymer.

9. The cosmetic care preparation as defined in claim 1, wherein said first component comprises a hydrophobic composition including at least one member selected from the group consisting of fats, oils and waxes.

10. The cosmetic care preparation as defined in claim 1, wherein said ready-to-use product comprises a hair care composition.

11. The cosmetic care preparation as defined in claim 1, wherein said ready-to-use product comprises a composition for care of skin and hair.

12. A two-component cosmetic care preparation consisting of a first component and a second component kept separate from the first component prior to application, wherein the first component and second component are not mixed to form a final, ready-to-use product until immediately prior to application;
wherein said first component includes at least one cationic surfactant and/or at least one cationic polymer and the second component has emulsifying or self-emulsifying properties and/or consistency-providing properties and the second component comprises at least one monoalcohol and/or at least one amphoteric or nonionic surfactant.

13. A two-component cosmetic care preparation consisting of a first component and a second component kept separate from the first component prior to application, wherein the first component and second component are not mixed to form a final, ready-to-use product until immediately prior to application;
wherein said first component comprises at least one saturated or unsaturated fatty acid glyceride or at least one silicone compound and at least one ester of a saturated or unsaturated fatty acid and a saturated or unsaturated fatty alcohol and the second component has emulsifying or self-emulsifying properties and/or consistency-providing properties and the second component comprises a cationic or anionic emulsion.

14. A method of caring for skin and hair, said method comprising the steps of:
a) providing a two-component cosmetic care preparation consisting of a first component and a second component kept separate from the first component prior to application, said first component including at least one conditioner and the second component having emulsifying or self-emulsifying properties and/or consistency-providing properties and comprising a cationic base emulsion or an anionic base emulsion, wherein the cationic base emulsion includes at least one lipophilic substance, at least one cationic emulsifier, at least one organic acid and water; and wherein the anionic base emulsion includes at least one lipophilic substance, at least one anionic emulsifier at least one organic acid and water;
b) mixing a predetermined amount of said first component with a predetermined amount of said second component to form a sufficient amount of a ready-to-use mixture for treatment of the skin and/or the hair immediately prior to application, wherein a ratio of said predetermined amount of said first component to said predetermined amount of said second component is in a range of from 20:1 to 1:20, whereby within said range relative proportions of said first component and said second component are adjusted to particular skin and/or hair type or quality of the hair and/or skin to which said ready-to-use mixture is to be applied; and
c) applying said sufficient amount of the ready-to-use mixture to the skin and/or the hair.

15. The method as defined in claim 14, further comprising admixing a colorant with said first component as an apportioning control for controlling relative proportions of said first component and said second component in said ready-to-use mixture.

16. The method as defined in claim 14, wherein said first component comprises a hydrophobic composition including at least one member selected from the group consisting of fats, oils and waxes.

17. The method as defined in claim 14, wherein said first component includes at least one member selected from the group consisting of anionic surfactants, cationic surfactants, amphoteric surfactants, nonionic surfactants, polymers, oils, fats and waxes.

18. A method of caring for skin and hair, said method comprising the steps of:
a) providing a two-component cosmetic care preparation consisting of a first component and a second component kept separate from the first component prior to application, said first component including includes at least one cationic surfactant and/or at least one cationic polymer and the second component has emulsifying or self-emulsifying properties and/or consistency-providing properties and the second component comprises at least one monoalcohol and/or at least one amphoteric or nonionic surfactant;
b) mixing a predetermined amount of said first component with a predetermined amount of said second component to form a sufficient amount of a ready-to-use mixture for treatment of the skin and/or the hair immediately prior to application, wherein a ratio of said predetermined amount of said first component to said predetermined amount of said second component is in a range of from 20:1 to 1:20, whereby within said range relative proportions of said first component and said second component are adjusted to particular skin and/or hair type or quality of the hair and/or skin to which said ready-to-use mixture is to be applied; and
c) applying said sufficient amount of the ready-to-use mixture to the skin and/or the hair.

19. The method as defined in claim 18, further comprising admixing a colorant with said first component as an apportioning control for controlling relative proportions of said first component and said second component in said ready-to-use mixture.

20. A method of caring for skin and hair, said method comprising the steps of:
- a) providing a two-component cosmetic care preparation consisting of a first component and a second component kept separate from the first component prior to application, wherein said first component comprises at least one saturated or unsaturated fatty acid glyceride or at least one silicone compound and at least one ester of a saturated or unsaturated fatty acid and a saturated or unsaturated fatty alcohol, and said second component has emulsifying or self-emulsifying properties and/or consistency-providing properties and said second component comprises a cationic or anionic emulsion;
- b) mixing a predetermined amount of said first component with a predetermined amount of said second component to form a sufficient amount of a ready-to-use mixture for treatment of the skin and/or the hair immediately prior to application, wherein a ratio of said predetermined amount of said first component to said predetermined amount of said second component is in a range of from 20:1 to 1:20, whereby within said range relative proportions of said first component and said second component are adjusted to particular skin and/or hair type or quality of the hair and/or skin to which said ready-to-use mixture is to be applied; and
- c) applying said sufficient amount of the ready-to-use mixture to the skin and/or the hair.

21. The method as defined in claim 20, further comprising admixing a colorant with said first component as an apportioning control for controlling relative proportions of said first component and said second component in said ready-to-use mixture.

22. A packaged product comprising a cosmetic care preparation, said cosmetic care preparation including a first component and a second component kept separate from the first component prior to application, said first component including at least one conditioner and the second component having emulsifying or self-emulsifying properties and/or consistency-providing properties and comprising a cationic base emulsion or an anionic base emulsion, wherein the cationic base emulsion includes at least one lipophilic substance, at least one cationic emulsifier, at least one organic acid and water; and wherein the anionic base emulsion includes at least one lipophilic substance, at least one anionic emulsifier at least one organic acid and water;

wherein said first component and said second component are contained spatially separately from one another but so that the first component is apportioned with the second component in variable, selectable or adjustable amounts.

23. The packaged product as defined in claim 22, wherein said cosmetic care preparation includes a third component separate from said first component and said second component, said third component consisting of cosmetic additives.

24. A packaged product comprising a cosmetic care preparation, said cosmetic care preparation including a first component and a second component kept separate from the first component prior to application, said first component including at least one cationic surfactant and/or at least one cationic polymer, the second component having emulsifying or self-emulsifying properties and/or consistency-providing properties and the second component comprising at least one monoalcohol and/or at least one amphoteric or nonionic surfactant;

wherein said first component and said second component are contained spatially separately from one another but so that the first component is apportioned with the second component in variable, selectable or adjustable amounts.

25. The packaged product as defined in claim 24, wherein said cosmetic care preparation includes a third component separate from said first component and said second component, said third component consisting of cosmetic additives.

26. A packaged product comprising a cosmetic care preparation, said cosmetic care preparation including a first component and a second component kept separate from the first component prior to application, wherein said first component comprises at least one saturated or unsaturated fatty acid glyceride or at least one silicone compound and at least one ester of a saturated or unsaturated fatty acid and a saturated or unsaturated fatty alcohol and the second component has emulsifying or self-emulsifying properties and/or consistency-providing properties and the second component comprises a cationic or anionic emulsion;

wherein said first component and said second component are contained spatially separately from one another but so that the first component is apportioned with the second component in variable, selectable or adjustable amounts.

27. The packaged product as defined in claim 26, wherein said cosmetic care preparation includes a third component separate from said first component and said second component, said third component consisting of cosmetic additives.

* * * * *